(12) United States Patent
Tseng et al.

(10) Patent No.: US 9,939,353 B2
(45) Date of Patent: Apr. 10, 2018

(54) APPARATUS FOR CELL OBSERVATION AND METHOD FOR CELL COLLECTION USING THE SAME

(71) Applicant: National Tsing Hua University, Hsinchu (TW)

(72) Inventors: Fan-Gang Tseng, Hsinchu (TW); Jui-Chia Chang, Hsinchu (TW); Tsung-Ju Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 232 days.

(21) Appl. No.: 14/668,344

(22) Filed: Mar. 25, 2015

(65) Prior Publication Data

US 2016/0061710 A1 Mar. 3, 2016

(30) Foreign Application Priority Data

Aug. 29, 2014 (TW) .............................. 103129843 A

(51) Int. Cl.
*G01N 15/14* (2006.01)
*G01N 1/28* (2006.01)
*G01N 15/10* (2006.01)

(52) U.S. Cl.
CPC ........... *G01N 1/2813* (2013.01); *G01N 15/14* (2013.01); *G01N 2015/1006* (2013.01)

(58) Field of Classification Search
None
See application file for complete search history.

(56) References Cited

U.S. PATENT DOCUMENTS

| 2006/0035311 A1* | 2/2006 | Goodwin, Jr. | ........ B01L 3/5027 435/34 |
| 2009/0170186 A1* | 7/2009 | Wu | .......... B03C 5/026 435/286.1 |

FOREIGN PATENT DOCUMENTS

| CN | 103339249 A | 10/2013 |
| TW | 201406953 A | 2/2014 |

OTHER PUBLICATIONS

A High Density Monolayer Cells Self-Assembly Chip for High-Throughput Rare Cells Detection, Tsung-Ju Chen et al., MEMS 2013, Taipei, Taiwan, Jan. 20-24, 2013.*
High-efficiency rare cell identification on a high-density self-assembled cell arrangement chip, Fan-Gang Tseng et al., Biomicrofluidics, May 12, 2014.*

* cited by examiner

*Primary Examiner* — Jill A Warden
*Assistant Examiner* — Julie L Tavares
(74) *Attorney, Agent, or Firm* — Muncy, Geissler, Olds & Lowe, P.C.

(57) ABSTRACT

An apparatus for cell observation and a method for cell collection using the same are disclosed. The apparatus for cell selection comprises a first substrate having an opening; and a second substrate having a photoresist unit disposed on a surface thereof, wherein the photoresist unit comprises at least one notch and defines a space which is interconnected with the notch and corresponds to the opening of the first substrate.

11 Claims, 3 Drawing Sheets

APPARATUS FOR CELL OBSERVATION AND METHOD FOR CELL COLLECTION USING THE SAME

CROSS REFERENCE TO RELATED APPLICATION

This application claims the benefits of the Taiwan Patent Application Serial Number 103129843, filed on Aug. 29, 2014, the subject matter of which is incorporated herein by reference.

BACKGROUND OF THE INVENTION

1. Field of the Invention

The present invention relates to an apparatus for cell observation and a method for cell collection using the same, and especially to an apparatus for cell observation, which is capable of achieving a simple, fast and accurate cell observation and a method for cell collection using the same.

2. Description of Related Art

A flow cytometry is currently the most widely used cell detection equipment in medical fields. The fluid system of a flow cytometry is based on a laminar flow or eddy-current to make the cells sequentially flow; and then the various parameters, such as the type, number and so on, of the cells flowing through the optical sensor are analyzed using light scattering and the fluorescent marker on the cell. In addition, a charge may be selectively applied to the passed cells, such that the passed cell will be deflected by action of the electromagnetic field and flow out from different exits for cell sorting. However, a flow cytometry is very expensive, bulky and complicated, and its operation and data analysis require intensive professional supervision, thereby limiting the universality.

Accordingly, in recent years, in the micro-electromechanical system (MEMS) field, a lot of researches with respect to the applications of the micro-fluid system have been conducted, intending to develop a small, fast, cheap and convenient chip for cell screening.

In the current studies, for example, numerous microcolumn arrays are provided on the microchannel, which is further modified with EpCAM antibodies thereon for the specific bonding between the antibodies and the antigens, so as to achieve the circulating tumor cell (CTC) screening. However, this method cannot completely capture all the CTCs in the sample, and the modification of antibodies is required at the stage of chip production, so that the versatility for various types of cells is reduced. Another example is the combination of dielectrophoresis and field-flow fractionation, in which the electrically neutral cells are polarized by a special electrolyte to migrate toward the direction of a high-intensity or low-intensity electric field. The disadvantage of this method lies in the special electrolyte which may cause damage to the cell, and the sorting method based on cell size easily causes error separation. A further example is to modify a magnetic ball with the antibodies first, and a magnetic field is then used to fix the magnetic ball, such that the sample to be tested can flows slowly through for cell collection. However, in order to obtain a high separation efficiency, the cell flow needs to be controlled at a very low speed (only by about tens to hundreds of cells per second), and therefore it is extremely time-consuming and impractical in the practical application.

In view of the above, it is desirable to provide a small-size, low-cost, easy-to-use sorting apparatus for cell observation with low cell loss and high cell versatility, which can be used to provide a precise cell observation in the sample, thereby achieving the follow-up purposes of cell culture and experiment.

SUMMARY OF THE INVENTION

An object of the present invention is to provide an apparatus for cell observation, such that the presence of the desired cells in the sample can be determined by a low-cost and easy way.

Another object of the present invention is to provide a method for cell collection, which is capable of rapidly culturing a sample containing the desired cells, thus reducing damage to cells to enable further use or study.

To achieve the above object, the present invention provides an apparatus for cell observation, comprising: a first substrate having an opening; a second substrate having a photoresist unit disposed on a surface thereof, wherein the photoresist unit comprises at least one notch and defines a space which is interconnected with the notch and corresponds to the opening of the first substrate; and a peripheral through hole disposed outside the photoresist unit.

Furthermore, the present invention also provides a method for cell collection, comprising: providing the above-described apparatus for cell observation; introducing a sample through the opening of the first substrate into the space defined by of the photoresist unit of the second substrate; adding a water absorbent material from the peripheral through hole; providing an optical system to observe one selected region of the sample; and placing the apparatus for cell observation in an incubator.

In the apparatus and method of the present invention, the first substrate and the second substrate may be made of any conventional biomaterial having high transparency and high compatibility (for example, glass), respectively, but the second substrate is preferably a conductive glass material, such as indium tin oxide (ITO) conductive glass. In addition, the first substrate and the second substrate are preferably disposed in parallel, but may be varied by a person skilled in the art depending on the practical demands, for example, an inclined arrangement at a specific angle, and the like. In addition, the shapes and sizes of the first substrate and of the second substrate are not particularly limited, and they may be designed with different shapes and sizes in consideration of cost or other factors. In a preferred condition, the first substrate and the second substrate have the same shape and size. The thickness of the first substrate is preferably 0.5 to 2 mm, and more preferably 1 to 2 mm; while the thickness of the second substrate is preferably 0.5 to 2 mm, and more preferably 0.5 to 1 mm. If those substrates are too thin, their mechanical strength may be insufficient; and if those substrates are too thick, they are unfavorable for observation through the optical system.

In the apparatus and method of the present invention, the first substrate and the second substrate are preferably separated from each other by the photoresist unit. The height of the photoresist unit (i.e., the height of the notch) is not particularly limited, and may be determined according to, for example, the desired cell types of the sample to be separated. In detail, the height of the photoresist unit may be less than the diameter of the cells to be separated, so as to restrict cell migration and prevent cells from outflow with liquid and loss. For example, when the cell to be separated has a diameter of 10 to 20 µm, the height of the photoresist unit may be 2 to 10 µm, 5 to 10 µm, or 8 to 10 µm. Furthermore, the sample may not necessarily contain living cells, but may include micron particles other than biological cells. A person skilled in the art may adjust the height of the photoresist unit depending on the requirements.

Furthermore, the width of the photoresist unit (i.e., the length of the notch) is basically not particularly limited, but may be adjusted to cope with the magnification of the microscope used or the number of the notches. Also, the width of the notch is not particularly limited, but is preferably 2 to 4 mm. If the width of the notch exceeds 4 mm, the cells in the sample may encounter the risk of overflow.

In addition, the shape of the photoresist unit is not particularly limited, but is preferably a shape without interior angles, such as circular ring, and elliptical ring, etc. When the photoresist unit has a shape with interior angles, for example, square annular, rectangular annular, and multi-angular annular, etc., the number of the notches at the interior angles is preferably greater than that at the other portions of the annular shape. This is because the sample may accumulate at the interior angles of the annular shape and become difficult to form a single cell array. Even though the apparatus can be inclined to avoid sample accumulation, the cells may still stick to the inner wall of the interior angles of the annular photoresist unit, resulting in poor observation. Also, the number of the notches of the photoresist unit is not particularly limited, but is preferably in even number. In addition, the notches thereof can be symmetrically arranged on the photoresist unit, to reduce the physical impact on the sample due to uneven force caused by, for example, rapid movement and so on.

In the apparatus and method of the present invention, the first substrate comprises a peripheral through hole which is disposed outside of the photoresist unit and separated therefrom by 5 to 10 mm, and preferably approximately the same as the diameter of the opening on the first substrate. The width of the peripheral through hole is 1 to 5 mm, through which any conventional powdered or liquid water absorbent material may be added, to increase the lateral pulling force to the sample from the notch of the photoresist unit, such that the sample can form a single cell array more quickly. Furthermore, the shape of the peripheral through hole is not particularly limited, but is preferably the same as the shape of the photoresist unit. For example, when the photoresist unit is circular, the peripheral through hole is also circular, except that the annular diameter of the peripheral through hole is greater than that of the photoresist unit.

In the apparatus and method of the present invention, the photoresist unit may be made of any conventional photoresist material, such as the typical positive photoresist or negative photoresist. The selection of the photoresist material may be determined according to the process factors or the material impact on the sample.

In the apparatus and method of the present invention, the shape and the size of the opening on the first substrate is not particularly limited, as long as it can facilitate introduction of the sample into the apparatus. For example, considering the droplet size under a typical operation, the opening may have a diameter of 3 to 10 mm, and is preferably a circular opening having a diameter of 4 to 8 mm. In the method of the present invention, the sample is preferably a flowable liquid or gel.

In the method of the present invention, after the sample is dropped, it enters the space defined by the photoresist unit only by fluid dynamics and the force of gravity. Meanwhile, the absorbent material added through the peripheral through hole applies a lateral pulling force to the sample, so that the cells in the sample are distributed as a single cell array in a single layer with high-density, thereby achieving the most compact arrangement and saving the space occupied by the sample. With the observation of an optical system (e.g., a microscope), the desired cells can be easily determined, and then the whole apparatus for cell observation is placed in an incubator for culture. Alternatively, the sample may also be marked through a pre-treatment depending on requirements, such as fluorescent labeling which utilizes the specificity between the antigens and antibodies, to facilitate cell observation in the optical system. Conventional methods, such as chemical modifications, fixations of modified magnetic beads with a magnetic field, fixations with an electric field by a DEP manner, and array formations by structural confinement, are either complicated, or need additional auxiliary equipment; and all of them cause loss in a large number of cells. In comparison, the method of the present invention can solve the above problems, and can be widely applied to various fields.

The apparatus of the present invention can be used with the conventional antigen-antibody reaction, biochemical test or optical system, to easily achieve the observation of physiological reaction of a large number of single cells, thereby achieving the purposes of drug test, cytotoxicity test, observation of the interactions between cells, or screening for trace amount of cells out of a large number of others. Furthermore, in tissue engineering, artificial cornea requires the employment of the monolayer of the corneal endothelial cells, and the monolayer cell array designed by this apparatus can be cultured into the corneal endothelial tissue in vitro, followed by transplant surgery to recover the transparency of corneal. In addition to the biomedical field, it also may be applied to the formation of a compact array of nanometer or micrometer beads, and further applied in a regular array structure. Therefore, it can be used to prepare a special planar structure for applications in optical, electrical and magnetic fields.

DETAILED DESCRIPTION OF THE PREFERRED EMBODIMENT

Figure 1:
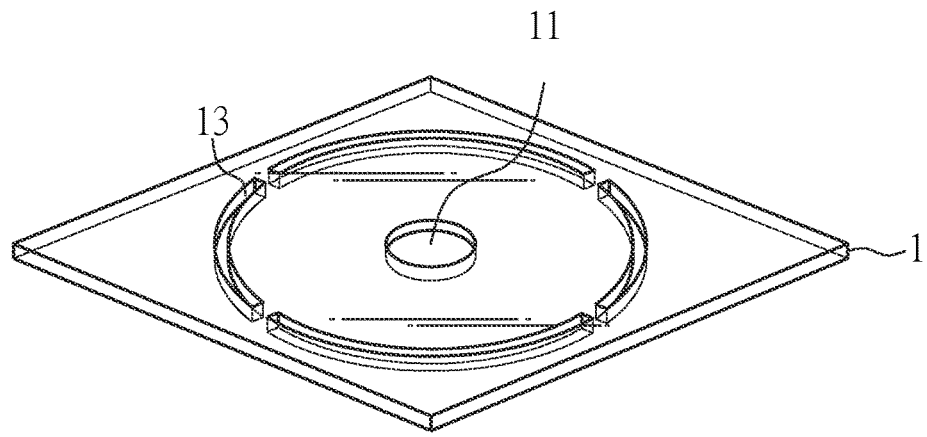
FIG. 1 shows the first substrate according to a preferred embodiment of the present invention.

FIG. 1 shows the first substrate according to a preferred embodiment of the present invention, which is an acrylic sheet having a length and a width of 2.5 cm and a thickness of about 1 to 2 mm. The opening 11 and the peripheral through holes 13 are formed in the acrylic sheet by physical methods such as drilling, laser cutting and so on, wherein the opening 11 has a diameter of about 3 to 10 mm and the peripheral through holes 13 respectively have a width of 2 to 4 mm and are separated from the opening 11 by a distance of 5 to 8 mm. The first substrate 1 may be modified with tridecafluoro-1,1,2,2-tetrahydrooctyl)trichlorosilane (FOTS), to prevent drops of the sample from overflow or buildup to avoid sample loss. In the present embodiment, the peripheral through holes 13 are designed as four arcuate through holes, which combine to form a circular ring.

Figure 2:
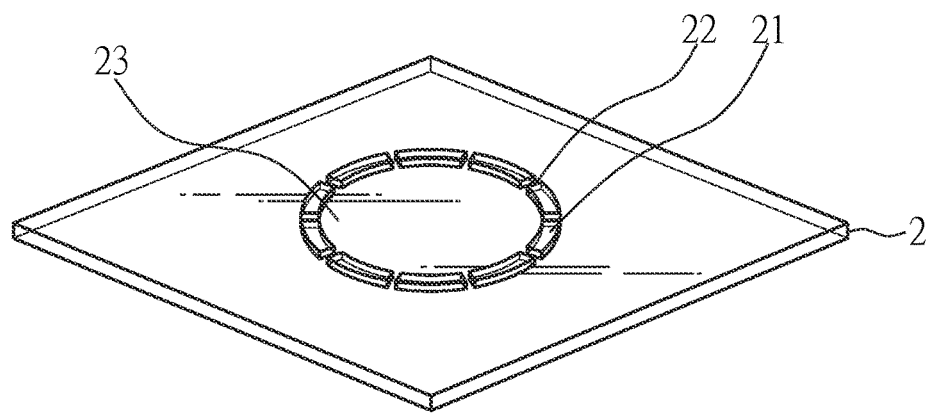
FIG. 2 shows the second substrate according to a preferred embodiment of the present invention.

FIG. 2 shows the second substrate according to a preferred embodiment of the present invention, which is an indium tin oxide (ITO) conductive glass having a length and a width of 2.5 cm and a thickness of about 0.5 to 1 mm. An annular photoresist unit 21 having a height of 2 to 10 μm, made of the negative photoresist SU-8, is disposed on the second substrate 2. The photoresist unit 21 has four notches 22 having a width of about 2 mm to define a space 23, and the space 23 is interconnected with the notches 22.

Figure 3:
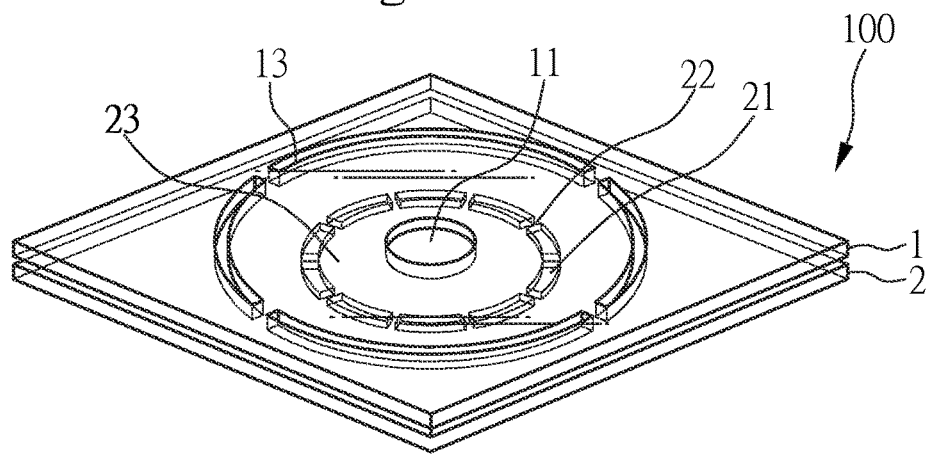
FIG. 3 shows the apparatus for cell observation according to a preferred embodiment of the present invention.

Referring to FIG. 3, the first substrate 1 of FIG. 1 is disposed above the second substrate 2 in FIG. 2, and the first substrate 1 and the second substrate 2 are disposed in parallel and separated from each other by the photoresist unit 21, and the space 23 corresponds to the opening 11 of the first substrate 1, thereby forming the apparatus for cell observation of the present invention. Both the photoresist unit 21 and the peripheral through holes 13 have a shape of circular ring. Upon assembling the first substrate 1 and second substrate 2, they can be fixed by the assistance of any conventional tool, to reduce the slip dislocation between the first substrate 1 and the second substrate 2. For example, at least one clamp may be used to clamp the edges of the first substrate 1 and the second substrate 2, but the present invention is not limited thereto.

Figure 4A:
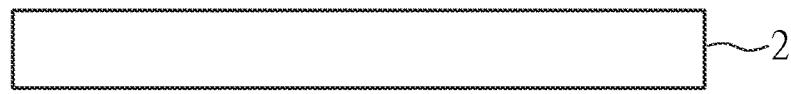
FIGS. 4A to 4C illustrate the preparation flow chart of the photoresist unit on the second substrate according to a preferred embodiment of the present invention.
Figure 4B:
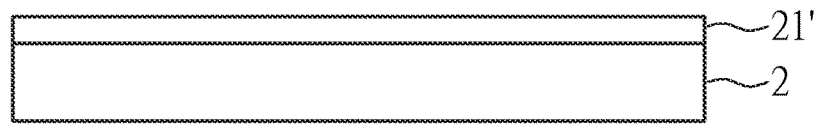
Figure 4C:
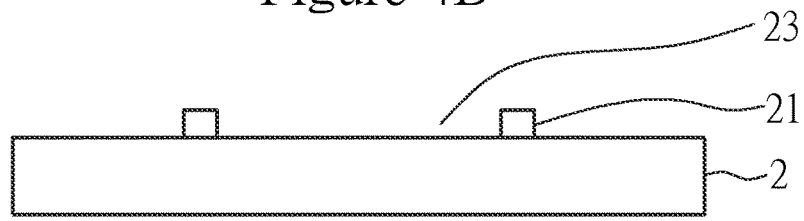
Figure 4D:
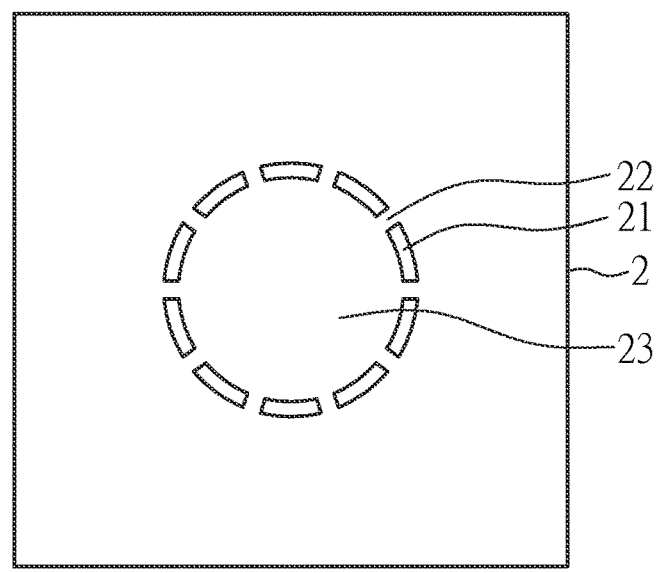
FIG. 4D is the top view of the second substrate in FIG. 4C.

More specifically, the second substrate 2 of FIG. 2 is prepared by the process as shown in FIGS. 4A to 4C. An indium tin oxide (ITO) conductive glass is provided, and the negative photoresist SU-8 is uniformly coated on the second substrate 2 to form a coating layer 21', followed by the exposure and development by the conventional photolithography technique, to form the photoresist unit 21, which has the top view as shown in FIG. 4D, wherein the photoresist unit 21 on the second substrate 2 has four notches 22 which define the space 23.

Figure 5:
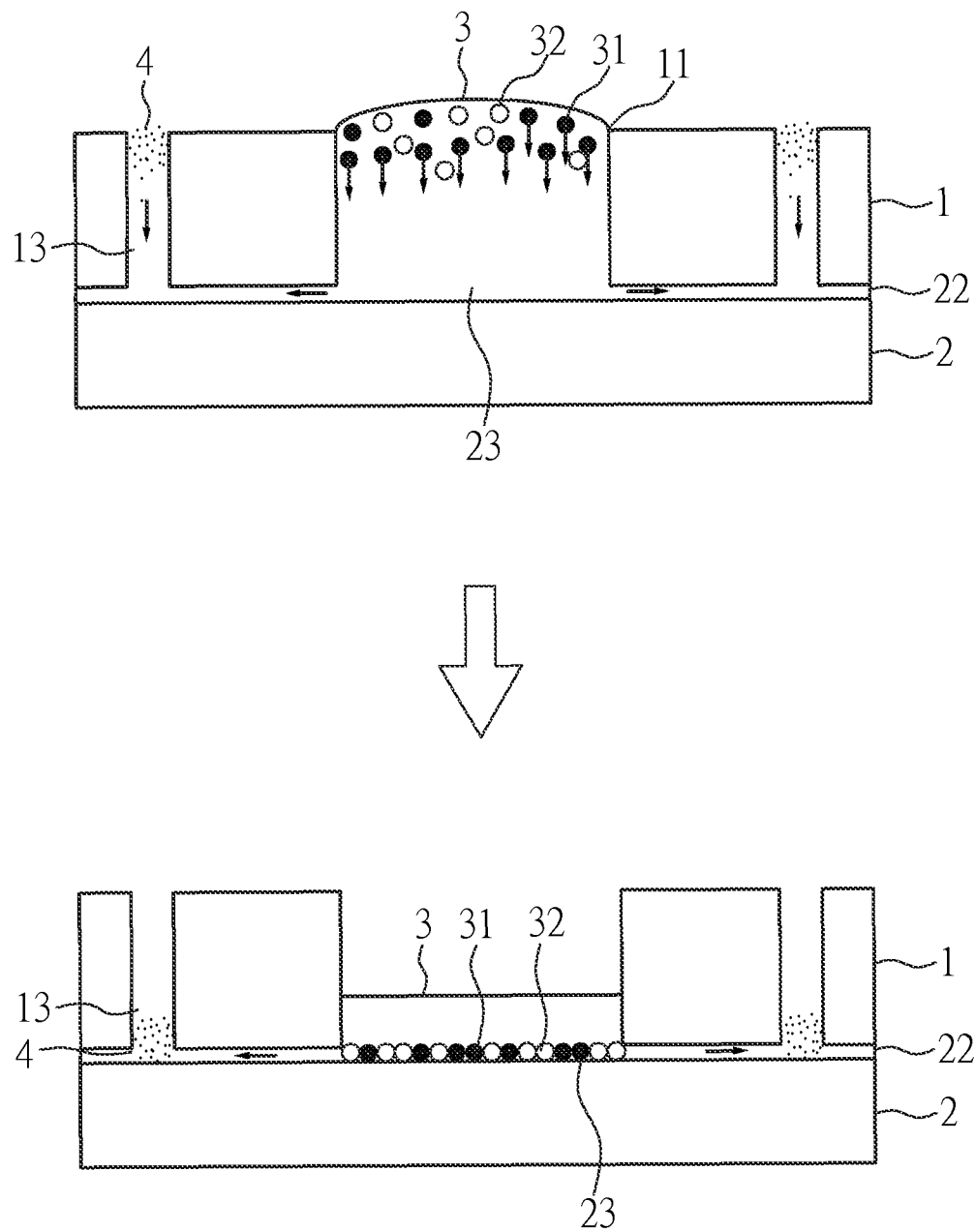
FIG. 5 is a schematic diagram showing the introduction of the sample into the apparatus for cell observation according to a preferred embodiment of the present invention.

FIG. 5 shows a schematic diagram of the introduction of the sample into the apparatus for cell observation of the present invention. In the present embodiment, since the cells 31, 32 are contained in the sample 3, upon assembling the first substrate 1 and the second substrate 2 (as shown in FIG. 3), an appropriate amount of a buffer solution (e.g., phosphate buffered saline (PBS)) may be first added dropwise into the space 23 defined by the photoresist unit of the second substrate 2, and then covered with the first substrate 1 to facilitate cell survival. Then, the sample 3, a liquid containing the unlabeled cells 31 and labeled cells 32, is added dropwise from the opening 11 on the first substrate 1, and introduced into the space 23 defined by the photoresist unit of the second substrate 2 downward by the gravity force (the direction indicated by the downward arrow). After that, the water absorbent material 4 (such as powdered polyphenylene acid (PAA)) is added into the peripheral through holes 13 to enhance the lateral pulling force on the cells in the sample 3 by a lateral fluid force thereof (the direction indicated by the lateral arrow), such that the cells in the sample 3 can rapidly form a single cell array in a single layer with high-density (it only takes 5 to 10 minutes from the dropwise addition of the sample to the formation of a single cell array after the apparatus is left standing). Next, the labeled cells 32 in the sample 3 are observed from the opening 11 by the microscope, and then the whole apparatus for cell observation is placed in an incubator for the subsequent experiments.

Thus, compared to the conventional technology, such as flow cytometry or cell chip screening, the apparatus and method for cell observation of the present invention have advantages of low cost, small size, easy operation, and low loss. Furthermore, the present invention has high versatility. It is able to perform the observation of a various types of cells simultaneously to facilitate the cell screening. In addition, almost all of the target cells in the sample can be captured, and therefore it is more suitable for application in the sample having only a small number of the target cells. Also, the method of the present invention requires less observation time, and high pressure, oil, or electrolyte is not directly applied to the cells, thus reducing the damage to cells. Therefore, accurate cell observation can be achieved. In addition, these cells can be directly used for the subsequent experiments after the culture, and thus cell death due to separation can be avoided.

In summary, the apparatus of the present invention is suitable for observation of reaction of a large number of single living cells, and may be used in studies of various aspects, such as drug tests, cytotoxicity tests, basic cell physiology researches, and the like, representing a significant advancement on biomedical research today.

Although the present invention has been explained in relation to its preferred embodiment, it is to be understood that many other possible modifications and variations can be made without departing from the spirit and scope of the invention as hereinafter claimed.

What is claimed is:

1. An apparatus for cell observation, comprising:
   a first substrate having an opening and a peripheral through hole;
   a second substrate having a photoresist unit disposed on a surface thereof, and
   a water absorbent material disposed in the peripheral through hole,
   wherein the photoresist unit comprises at least one notch and defines a space which is interconnected with the notch and corresponds to the opening of the first substrate,
   wherein the first substrate is disposed above the second substrate, the first substrate and the second substrate are separated from each other by the photoresist unit, and the peripheral through hole is disposed outside the photoresist unit.

2. The apparatus of claim 1, wherein the peripheral through hole and the photoresist unit are spaced apart by 5 to 10 mm.

3. The apparatus of claim 1, wherein a width of the peripheral through hole is 1 to 5 mm.

4. The apparatus of claim 1, wherein the second substrate is an indium tin oxide (ITO) conductive glass.

5. The apparatus of claim 1, wherein a thickness of the second substrate is 0.5 to 2 mm.

6. The apparatus of claim 1, wherein the first substrate and the second substrate are disposed in parallel.

7. The apparatus of claim 1, wherein the photoresist unit is made of a negative photoresist.

8. The apparatus of claim 1, wherein the photoresist unit is an annular photoresist unit.

9. The apparatus of claim 1, wherein a height of the photoresist unit is 2 to 10 μm.

10. The apparatus of claim 1, wherein a width of the notch is 2 to 4 mm.

11. A method for cell collection, comprising:
    providing the apparatus for cell observation of claim 1;
    introducing a sample through the opening of the first substrate into the space defined by of the photoresist unit of the second substrate;

adding a water absorbent material through the peripheral through hole;
providing an optical system to observe a selected region of the sample; and
placing the apparatus for cell observation in an incubator.

* * * * *